United States Patent [19]

Houston

[11] 4,047,041

[45] Sept. 6, 1977

[54] X-RAY DETECTOR ARRAY

[75] Inventor: John M. Houston, Schenectady, N.Y.

[73] Assignee: General Electric Company, Schenectady, N.Y.

[21] Appl. No.: 678,074

[22] Filed: Apr. 19, 1976

[51] Int. Cl.² .............................................. G01T 1/18
[52] U.S. Cl. ................................... 250/385; 250/374; 250/445 T
[58] Field of Search ............... 250/385, 445 T; 313/93

[56] References Cited

U.S. PATENT DOCUMENTS

| 2,489,133 | 11/1949 | Herzog ................................... 313/93 |
| 2,692,948 | 10/1954 | Lion ........................................ 313/93 |
| 3,418,474 | 12/1968 | Spergel et al. ......................... 250/385 |
| 3,930,162 | 12/1975 | Reiss ....................................... 250/385 |
| 3,991,312 | 11/1976 | Whetten et al. ....................... 250/385 |

Primary Examiner—Harold A. Dixon
Attorney, Agent, or Firm—Jack E. Haken; Joseph T. Cohen; Jerome C. Squillaro

[57] ABSTRACT

An ionization chamber array, useful in computerized X-ray tomography apparatus comprises a plurality of substantially parallel, rod-like cathodes disposed equidistant between parallel planar anodes in a high pressure detector gas. X-ray energy enters the array in the plane of the cathodes in a direction substantially parallel to their long dimensions.

9 Claims, 10 Drawing Figures

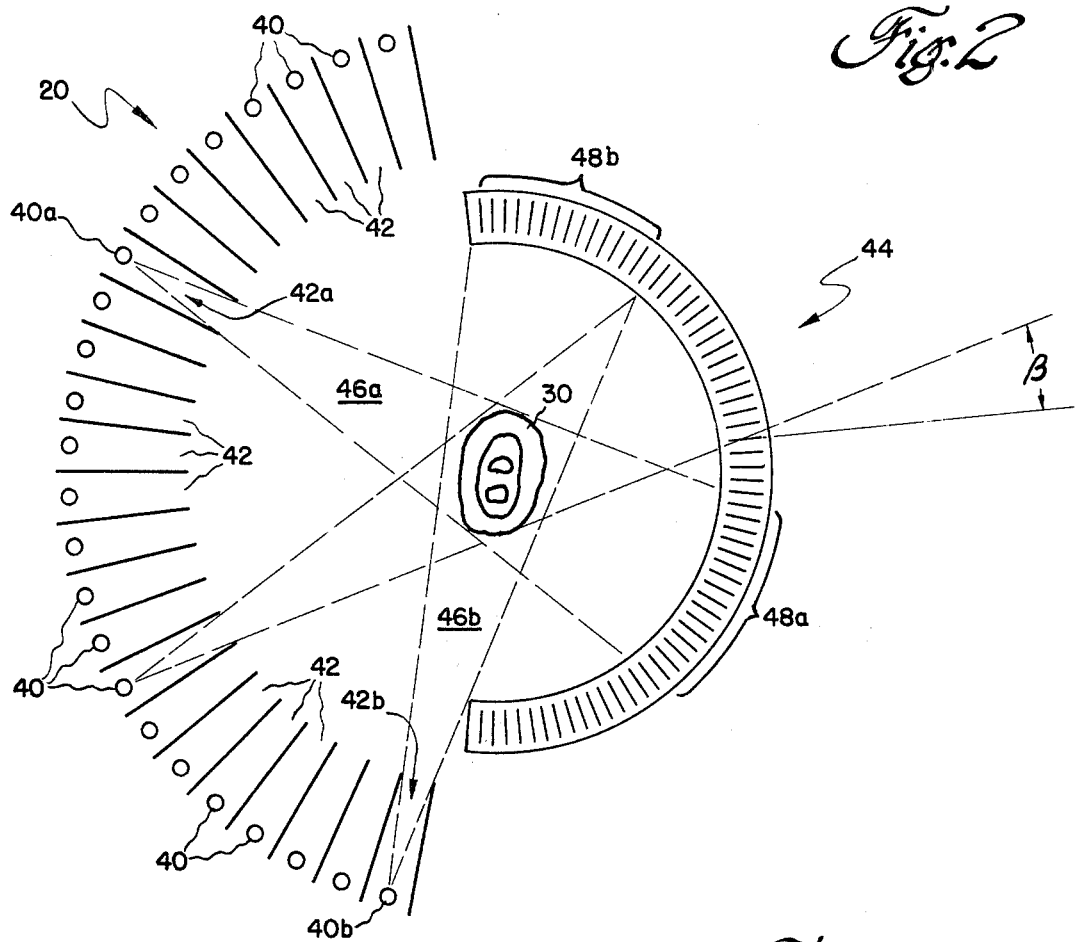
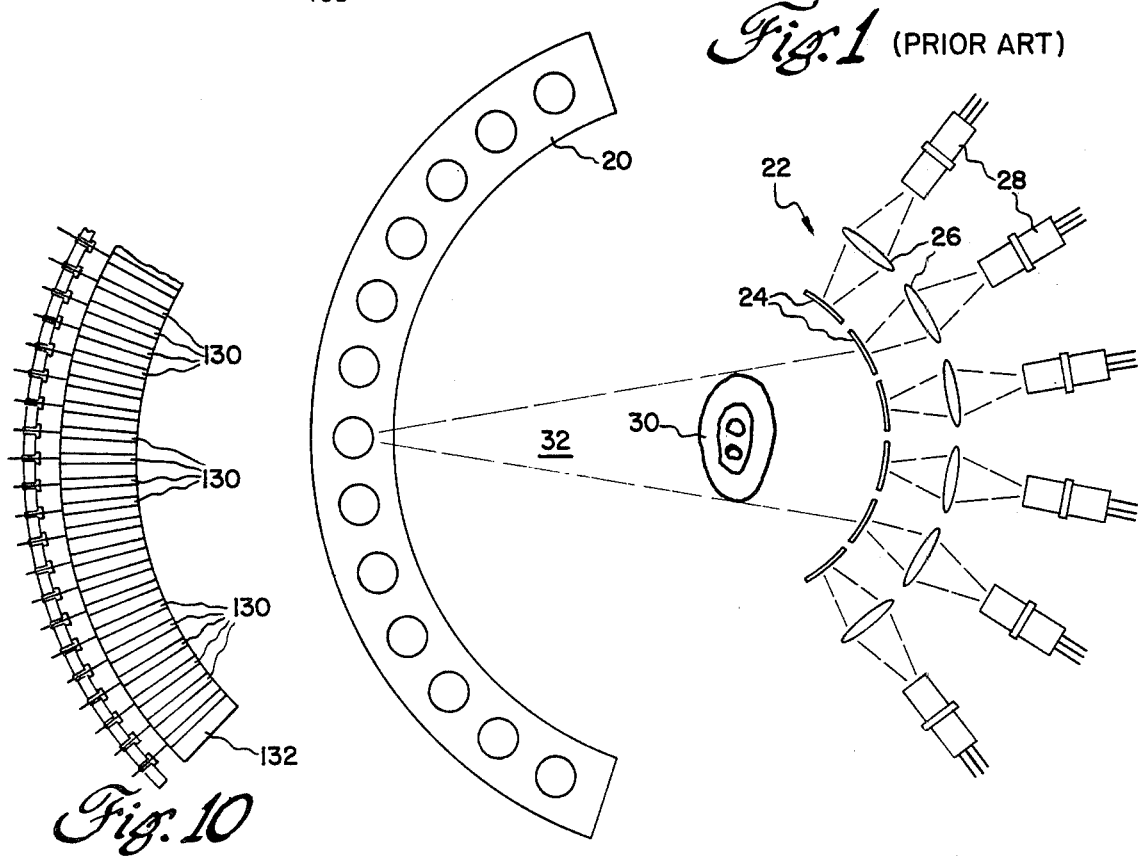

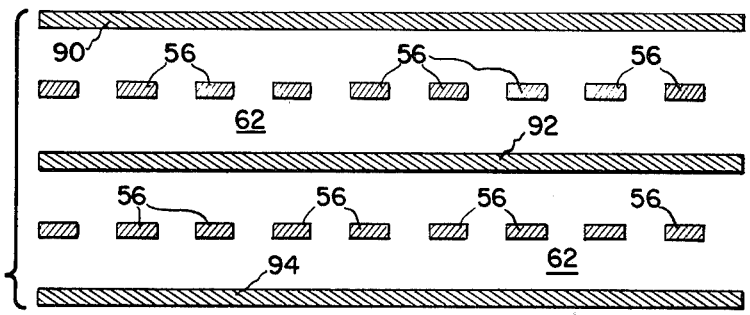
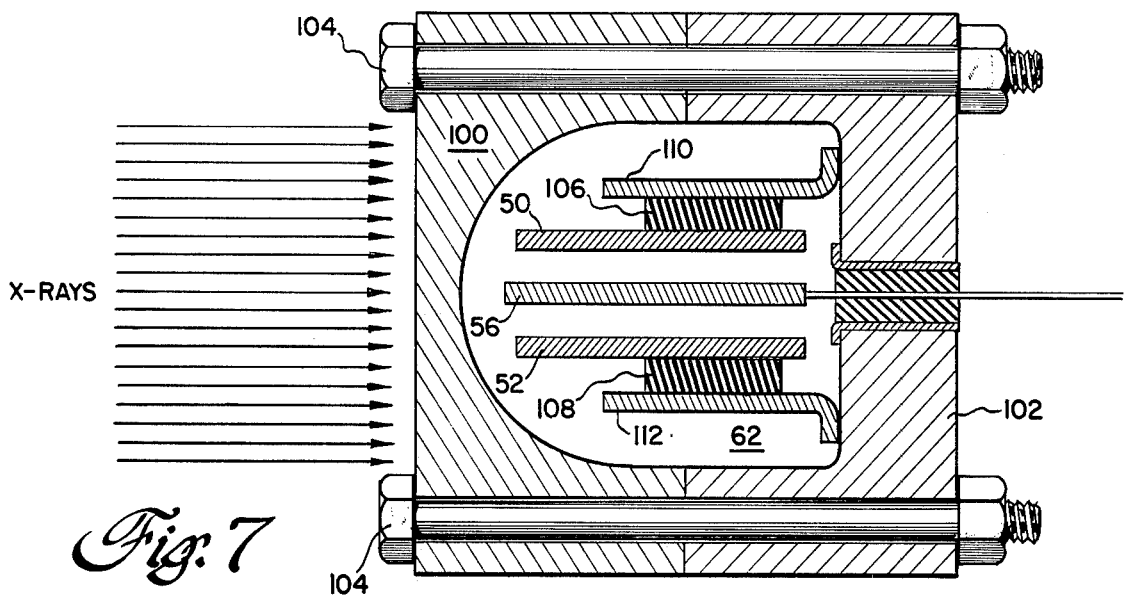
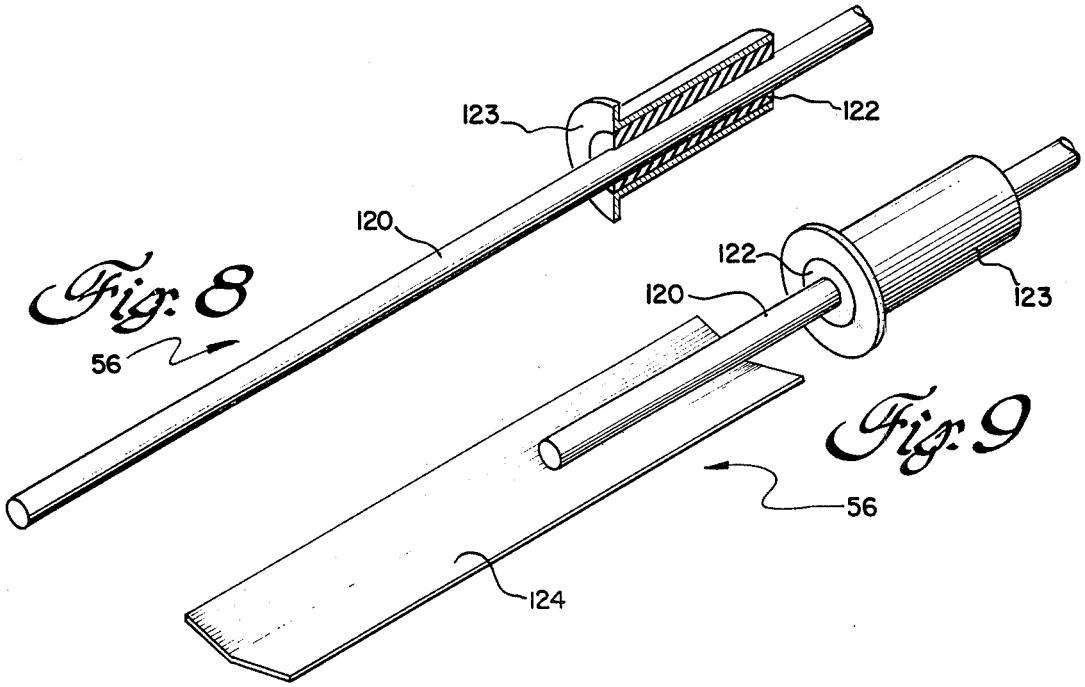

X-RAY DETECTOR ARRAY

The invention relates to ionization chamber, x-ray detector arrays for use with high speed, computerized, tomographic imaging apparatus. More particularly, the invention relates to ionization chambers comprising planar arrays of substantially parallel collector electrodes wherein incident x-rays enter the detector in a plane substantially parallel to the electrode elements.

BACKGROUND OF THE INVENTION

Computerized x-ray tomography produces images of internal body organs which are free from the shadow of intervening structures. Prior art tomographic equipment, has generally, comprised an x-ray source disposed opposite one or more x-ray detectors on a movable structure. The source and detectors rotate and/or translate in a plane through the body organs undergoing examination to produce electrical signals, representative of views along a plurality of ray paths. The signals are then combined, usually in digital computer equipment, to reconstruct shadow-free images of internal body sections. Tomography equipment of this type is described, for example, in U.S. Pat. No. 3,778,614 to Hounsfield.

The rate of production of images in a tomography system which incorporates moving sources and detectors is necessarily limited by the time required to accomplish the physical translation or rotation of the mechanism and is, typically, limited to less than one image per second. Such equipment is, therefore, unsuited for producing moving pictures of body organs, for example, of a beating heart. Dr. Earl Wood of the Mayo Clinic has recently proposed a tomographic system for imaging moving body organs wherein a plurality of x-ray sources are sequentially pulsed to rapidly produce x-ray transmission data along a number of diverse ray paths.

The x-ray detectors utilized in prior art x-ray tomography apparatus have generally comprised scintillation crystals or phosphor screens coupled to optical detectors, for example, image orthicon or photomultiplier tubes. Such devices are rather large and must, generally, be utilized with collimation apparatus to achieve fine spatial resolution. Such scintillation detectors and collimation apparatus are, relatively inefficient detectors of x-ray energy. It is, therefore, necessary to expose a patient undergoing tomographic examination in such equipment to a relatively high dose of ionizing radiation.

My copending patent application Ser. No. 616,930, filed Sept. 26, 1975, with Nathan R. Whetten describes a high pressure, xenon filled ionization chamber array which is characterized by high detection efficiency and fine spatial resolution when utilized in x-ray tomography equipment. The detector comprises a large plurality of detector cells separated by substantially parallel metal collector plates which may be focused on a single source of diverging x-rays. X-ray photons entering the detector cells produce ion-electron pairs which drift under the influence of an electric field, in a direction parallel to the line of the detector array and substantially perpendicular to the direction of the incident x-ray beam, to the collection plates. Detectors of this type are well suited for the efficient detection of diverging x-ray energy which, for example, may be produced from a single x-ray source and collimated to provide a planar, fan-like spatial distribution. The ion chamber array of that disclosure is, however, relatively inefficient for detecting x-ray energy which originates from an array of spatially separated x-ray sources of the type utilized in the above-described, high speed tomographic equipment.

SUMMARY OF THE INVENTION

In accordance with the present invention, high speed x-ray tomography apparatus comprises an array of spatially separated, collimated x-ray sources disposed opposite an array of closely spaced x-ray detectors. Each of the x-ray sources is collimated to produce a relatively narrow, planar, sectorial swath of x-ray photons. Sets of x-ray sources in the array are pulsed simultaneously to obtain x-ray transmission data for tomographic image reconstruction. The collimation and grouping of the x-ray sources as well as the sequence of firing is chosen so that each source in a set illuminates a separate and distinct sector of the x-ray detector array. The time required to produce a tomographic image is thereby reduced.

An ionization chamber array suitable for use in this tomographic equipment comprises a comb-like array of collector electrodes of a first polarity disposed equi-distant between two parallel sheet elelctrodes of the opposite polarity and immersed in a high pressure, ionizable gas. X-ray energy enters the detector in a direction substantially parallel to the comb-like electrodes and interacts with the detector gas to produce electron-ion pairs. The electrons and ions drift under the influence of an electric field, in a direction substantially perpendicular to both the direction of the incident x-ray beam and the linear array direction, to the collection electrodes. The detector cells of the present array are not focused on a single x-ray source, as were the cells of the array described in the above-referenced patent disclosure, and are therefore well suited for use in tomography systems having multiple, spatially distributed, x-ray sources.

It is, therefore an object of this invention to provide high speed ionization chamber arrays which are efficient for detecting x-rays from multiple spatially separated sources.

Another object of this invention is to provide a linear array of ionization chambers wherein electron and ion flow is perpendicular to both the direction of an incident x-ray beam and the line of the array.

BRIEF DESCRIPTION OF THE DRAWINGS

The novel features believed characteristic of the present invention are set forth in the appended claims. The invention itself, together with further objects and advantages thereof, may be best understood with reference to the following detail description of the preferred embodiment taken in connection with the appended drawings in which:

FIG. 1 is a high speed tomography system of the prior art;

FIG. 2 is a high speed tomography system of the present invention;

FIG. 6 is an alternate embodiment of the ionization chamber of the present invention providing high speed operation;

FIG. 7 is an alternate embodiment of an ionization chamber of the present invention;

FIG. 8 is a collection electrode for use in the ionization chambers of FIGS. 4, 5, 6, and 7;

FIG. 9 is an alternate embodiment of the collection electrode of FIG. 8; and

FIG. 10 is an alternate structure for collecting electrodes in ion chamber arrays of the present invention

DESCRIPTION OF THE PREFERRED EMBODIMENT

Figure 3:
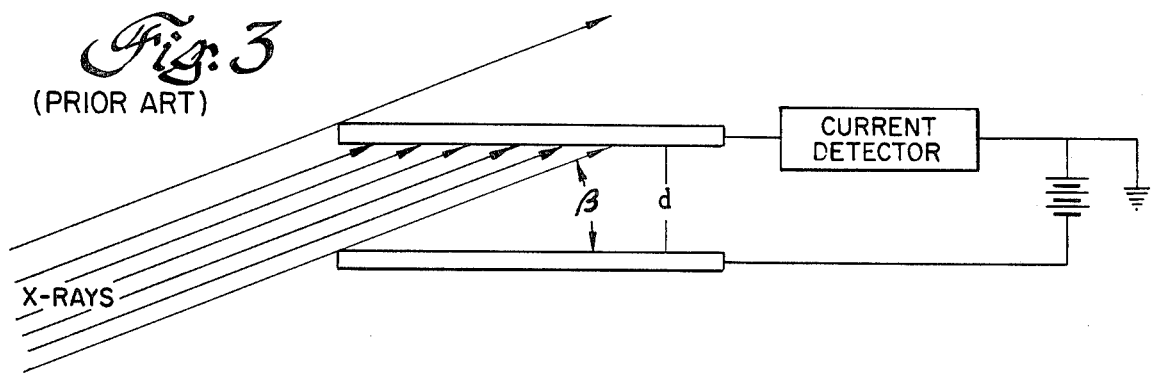
FIG. 3 is a single detector cell of the prior art.

FIG. 1 illustrates a high speed x-ray tomography system of the prior art. An array of pulsed x-ray sources 20 is disposed opposite an array of x-ray detectors 22. Each individual x-ray detectors of the array 22 comprises a phosphor screen 24 adapted to emit light in proportion to incident x-ray intensity. light from the screen 24 is focused by a lens 26 on a television camera type pick-up tube, typically an image orthicon 28. Electrical signals, from each tube 28, which represent a linear distribution of x-ray intensities across the width of a screen 24, are transmitted to a digital computer for processing into x-ray tomographic images.

Body structures 30 undergoing examination are interposed between the source array 20 and the detector array 22. Individual x-ray sources in the array 20 are sequentially pulsed to produce swaths of ionizing radiation 32 which are attenuated in varying degrees by the body structure 30 and impinge on the detector array 22. The elements of the array 20 may be pulsed in rapid sequence to provide x-ray transmission information for a plurality of intersecting paths through the body structure 30 from which image information may be constructed. Each source in the array 20, however, necessarily illuminates substantially the entire detector array 22 and the rate of sequential pulsing of the individual source is, therefore, necessarily limited by the speed at which data may be read from the detector elements through the pick-up tubes 28. information produced by a single pulse must be completely read out from a detector tube 28 before another source in the array 20 is pulsed in order to eliminate a redundancy of information which would occur if x-rays from two sources reached the same tube during a single readout.

FIG. 2 is an improved high speed tomography system of the present invention. A substantially semicircular array of x-ray sources 20 comprises a plurality of individual x-ray tube anodes 40 separated by an array of collimators 42. The collimators 42 are shaped so that the x-ray beam from each anode 40 is restricted to a substantially planar, sectorial swath. X-ray energy in the swath passes through a body structure 30 and impinges on a curvilinear array of closely spaced, ionization chamber, detectors 44 disposed in the plane of the x-ray swath. The dimensions and geometry of the collimators 42 are chosen to limit the width of the x-ray swath so that it illuminates a relatively small sector of the array 44. Thus, in the illustration of FIG. 2, x-rays from anode 40a pass through collimator 42a to form a sectorial swath 46a which impinges on a small subgroup 48a of detectors in the array 44. Likewise, x-rays from the anode 40b pass through the collimator 42b and impinge on a separate and distinct group 48b of detectors in the array 44.

The x-ray sources in the array 40 are pulsed in sets, the sources in each set being chosen so that the individual sources illuminate separate and distinct groups of detectors in the array 44. After each set of sources is pulsed, data from the detector 44 is read out into a digital computer for processing and another set of sources, similarly chosen to illuminate distinct detector groups is pulsed. Depending on the collimator geometry and the number of detectors and sources in the arrays, the speed of image processing may be increased by a factor of 2 or more.

The detector array 44 may comprise ionization chambers of the type described in the above-mentioned U.S. patent application, Ser. No. 616,930, which is incorporated herein, by reference, as background material. That detector comprises an array of detector cells defined between individual sheet collector electrodes which are disposed substantially parallel to the direction of the incident x-ray beam and perpendicular to the plane of the x-ray swath. The individual cells of such a detector are focused on a sigle source to provide high efficiency x-ray collection and detection, and such a detector is well suited for use in conventional tomography apparatus which comprises a single x-ray source. When used in a multiple source tomography system, this array suffers from a substantial loss of detection efficiency for x-rays which originate off the focal point of its individual cells. The cause of this inefficiency may be noted by reference to FIG. 2 and FIG. 3 which is an enlarged view of an indivual detector cell illuminated by the x-rays from a source lying outside its focal region and incident on the plane of the cell at an angle $\beta$. If R is the radius of the detector arc and P is the radius of the field of view at the body 30, the maximum value of the angle $\beta$ occurs at the edge of each view such that $\sin \beta = P/R$. In a typical system of the type illustrated in FIG. 2 used, for example, for viewing a beating heart, P equals approximately 20 centimeters and R equals approximately 75 centimeters, yielding a maximum angle, $\beta$, of 16°. The efficiency of the cell for oblique detection angles is determined by the spacing of the collector electrodes $d$. The spacing $d$ is determined, among other factors, by the degree of spatial resolution required by the system and by the time required for the electrons and ions produced within a cell to drift under the influence of an electric field to the individual electrons. If, for example, the cell is filled with a xenon detector gas at a pressure of approximately 20 atmospheres, a spacing, $d$, of approximately 1 mm is required to obtain a 1 millisecond response time. The response of such a cell, with 1 millimeter electrode spacing, for x-rays incident at an angle $\beta$ of 16° will be only approximately 14 percent of its efficiency for x-rays incident at an angle of 0°. This loss of efficiency introduces serious calibration problems into image reconstruction algorithms and necessarily increases the radiation dose which is required to produce an image of given resolution. The calibration problem in a multiple source array is, of course, greatly increased by the fact that the angle of incidence of x-rays on each cell is different for each detector and large numbers of calibration factors must, therefore, be stored and utilized.

Figure 4:
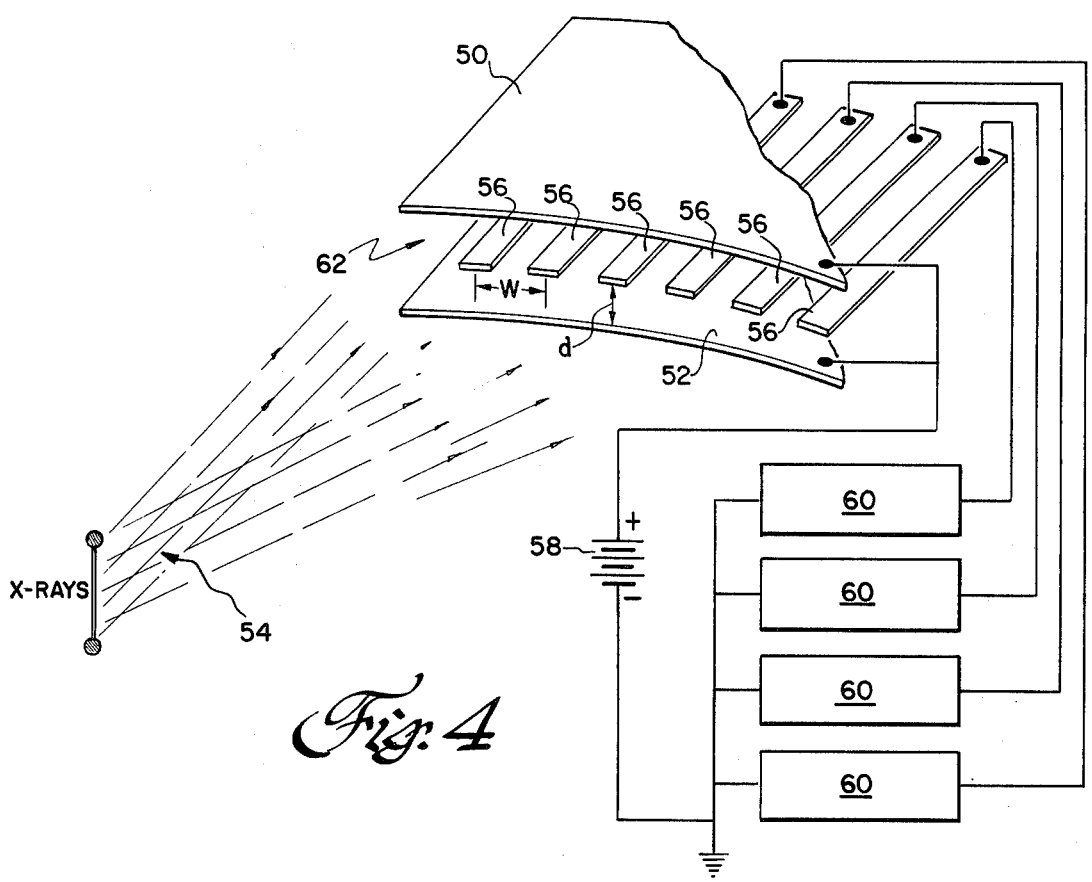
FIG. 4 is an ionization chamber array of the present invention.

FIG. 4 is an ion chamber array of the present invention which has a substantially constant detection efficiency for varying angles of x-ray incidence. A pair of planar, conductive anodes 50 and 52 are disposed parallel to an incident sheet of x-ray radiation 54. A plurality of rod-like cathodes 56 are disposed, equi-distant between the anodes 50 and 52 and substantially parallel, one to the other, with their longest dimension generally parallel to the incident x-rays. One terminal of a voltage source 58 is connected to the anode sheets 50 and 52. Each of the cathodes 56 is connected through one of a plurality of current detector circuits 60 to the other terminal of the voltage source 58. In a preferred embodiment of the invention, a common node of the voltage source and the current detectors represents ground potential.

It will be recognized, by those skilled in the art, that the polarity of the voltage source and the position of the ground connection may be varied without affecting the utility of the invention and that the designation of the collection electrodes 50, 52, and 56, as anodes and cathodes is for ease of description only.

A detector gas 62 fills the space between the anode sheets 50 and 52 and the cathodes 56. The gas type, gas pressure, and the spacing W between the electrodes are chosen using methods well known to the art so that a large fraction (typically more than 70 percent) of the incident x-ray photons are absorbed within the gas. The detector gas 62, typically comprises rare gas of high atomic number, for example, xenon, krypton, argon, or a molecular gas comprising atoms having an atomic weight greater than that of argon (i.e., 39.9); at a pressure in the range from approximately 10 atmospheres to approximately 100 atmospheres.

Incident x-rays 54 interact with the detector gas 62 between the anodes 50 and 52 to produce electron-ion pairs. The electrons drift under the influence of the electric field, imposed by the voltage source 58, to the anode plates 50 and 52 while the ions are similarly collected on the cathodes 56. Ion current flow to any individual cathode 56 is proportional to the number of interactions between photons and gas atoms in the region of that cathode so that the distribution of current flow among the individual current detector circuits 60 of the array is a function of the distribution of x-ray intensity along the detector array. The direction of electron and ion motion within the detector is substantially perpendicular to the array length and to the incident x-ray beam.

The cathodes 56 may be arrayed parallel one to the other to produce a linear detector array. Alternately, the detectors may lie at small angles, one to the other, to define a curved or semicircular array of the type illustrated in FIG. 2.

Figure 5:
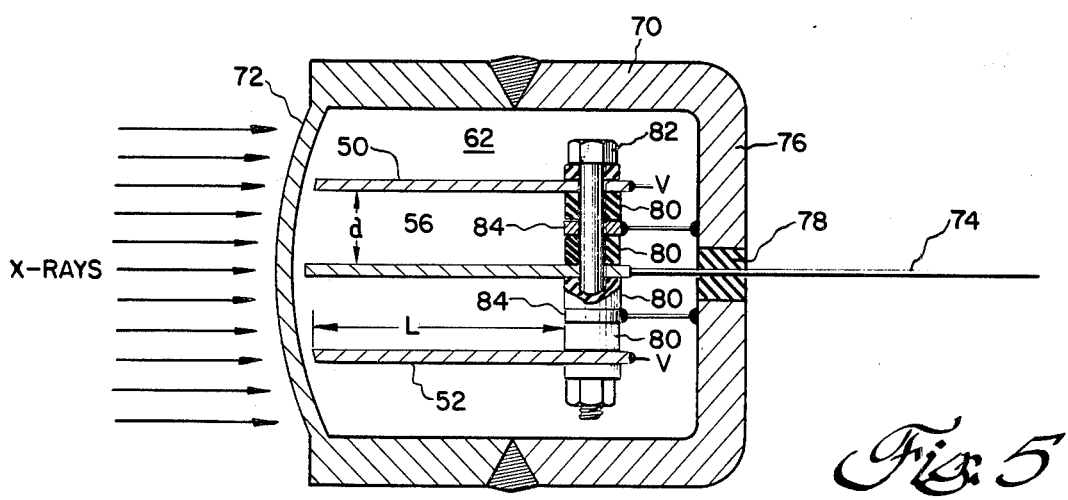
FIG. 5 is a side view of an ionization chamber array of the present invention.

FIG. 5 illustrates a preferred detector embodiment. An outer jacket 70, which may typically be formed from welded aluminum, contains the detector gas 62. One face of the jacket forms a thin curved window 72. The window thickness and material are chosen so that the absorption of x-rays in the window 72 is substantially less than the absorption of x-rays within the gas 62. A plurality of rigid wires 74 penetrate a face 76 of the jacket 70 opposite the window 72. Each of the wires 74 is insulated from the jacket 70 with a dielectric insert 78, which may typically comprise epoxy resin. The cathodes 56 are attached, typically by welding, by the wires 74 in a plane substantially parallel to an incident x-ray beam and perpendicular to the window 72. The anodes 50 and 52 are separated from the cathode 56 by insulators 80 and are supported by an insulated or electrically non-conducting bolt 82. Grounded guard rings 84 may be inserted in the insulators 80 between the anodes 50 and 52 and the cathodes 56 to drain leakage currents which might otherwise flow through the current detector circuits and introduce errors therein. The optimum length L of the anodes and cathodes along the incident x-ray beam is a function of the gas pressure with in the housing. For xenon detector gas at a pressure of 20 atmospheres, an electrode length L of approximately 2.5 centimeters is optimum. If the xenon pressure is raised to 50 atmospheres, the optimum electrode length may be reduced to approximately 1 centimeter. In general, a high gas pressure (for example, on the order of 50 atmospheres) is desirable since it allows smaller detector dimensions and thus tends to reduce microphonic vibrations and associated error currents. High gas pressure also tends to reduce crosstalk between the array elements which might be caused by xenon characteristic radiation.

The gap between the electrodes and cathodes $d$ (FIG. 3) determines the response time of the detector. For thick x-ray sheets, the electrode spacing and response time may be maintained at small values by stacking several arrays of cathodes 56 between three or more anode plates 90, 92, and 94 (FIG. 6).

FIG. 7 illustrates an alternate embodiment of the detector construction wherein the jacket comprises two halves 100 and 102, retained by bolts 104. The anodes 50 and 52 of this embodiment may be supported on insulated blocks 106 and 108 attached to metal straps 110 and 112 which are welded to the back wall of the detector jacket half 102.

FIG. 8 is a cathode 56 embodiment which is useful in the detector of FIG. 7. The cathode element comprises a stiff metallic rod 120 which is attached to the back wall of the detector jacket and supported by an insulator 122 which may, for example, comprise epoxy resin. The insulator 122 may, if desired, be contained in a metal header 123 to facilitate attachment to the jacket wall.

FIG. 9 is an alternate embodiment of a cathode 56 element useful in the detector of FIG. 7. The cathode in this embodiment comprises a flat blade of metal 124 which is bonded, for example by welding, to a stiff metal rod 120 which is supported by an insulator 122 and a header 123 in the same manner as the cathode rod of FIG. 8. If desired, the blade 124 may be creased to provide structural rigidity and reduce microphonic vibrations.

FIG. 10 is an alternate cathode embodiment which is useful in the detectors of FIG. 5 and FIG. 7. The cathode elements comprise a plurality of metallic strips 130 which are bonded to the surface of a dielectric sheet 132. The metallic strips 130 may be applied to the sheet 132 in any conventional manner, for example, by screen printing, etching laminated printed circuit board material, or vapor deposition. The dielectric sheet 132 may, for example, comprise reinforced epoxy resin, ceramic, or any other material commonly used for that purpose in detector arts.

The cathode embodiment of FIG. 10 is particularly useful in that the number of individual parts required is significantly reduced, compared to other large scale detector arrays, and the spacing between the cathode elements may be rigidly maintained to reduce microphonic signals.

The detector of the present invention allows highly efficient and accurate measurement of x-ray intensity, particularly in geometries where x-rays originate from spatially separated sources. The use of a high pressure detecting gas allows construction of a compact, rigid ion chamber array which has a low parts count per detector cell and which is suitable for semi-automated production.

While the invention has been described in detail herein in accord with certain preferred embodiments thereof, many modifications and changes therein may be effected by those skilled in the art. Accordingly, it is intended by the following claims to cover all such modifications and changes as fall within the true spirit and scope of the invention.

The invention claimed is:

1. An ion chamber detector array for determining the distribution of x-ray intensities in one or more flat, coplanar, x-ray beams comprising:

a first flat anode sheet disposed in a plane lying parallel to the plane of said x-ray beams;

a second, flat anode sheet disposed parallel to said first anode sheet, a third, flat anode sheet disposed parallel to and adjacent a side of said first anode sheet opposite said second anode sheet;

a first plurality of rod-like cathode elements disposed in said x-ray beam and equi-distant between said first anode sheet and said second anode sheet, a long dimension of said cathode elements being oriented in a direction substantially parallel to the angle of incidence of one or more of said x-ray beams;

a second plurality of rod-like cathode elements disposed in said x-ray beam and equi-distant between said first anode sheet and said third anode sheet, a long dimension of said cathode elements being oriented in a direction substantially parallel to the angle of incidence of one or more of said x-ray beams;

a gaseous detecting medium disposed between said first anode sheet, and second anode sheet, said third anode sheet, and said cathodes;

means for applying an electric potential between said cathodes and said anodes, whereby an electric field is impressed between said cathodes and said anodes, and for connecting each of said cathodes to a signal processing circuit.

2. The detector array of claim 1 wherein said cathode elements are parallel, one to the other.

3. The detector of claim 1 wherein said gaseous medium comprises elements of atomic weight greater than or equal to the atomic weight of argon.

4. The detector arrayd of claim 3 wherein said gaseous medium is selected from the group of gases consisting of argon, krypton, xenon, and mixtures thereof.

5. The detector of claim 4 wherein said gaseous medium is xenon.

6. The detector of claim 1 wherein said gaseous detecting medium has a pressure between approximately 10 atmospheres and approximately 100 atmospheres.

7. The detector of claim 6 further comprising a pressure vessel disposed about and containing said anodes, said cathodes, and said gaseous medium.

8. The detector of claim 7 wherein said pressure vessel comprises a window lying perpendicular to and adjacent said anodes and said cathodes.

9. The detector of claim 1 wherein said cathode elements comprise strips of electricity conductive material disposed on a sheet of dielectric material.

* * * * *